(12) United States Patent  
Kang et al.

(10) Patent No.: US 9,238,637 B2
(45) Date of Patent: Jan. 19, 2016

(54) STABLE POLYMORPHIC FORMS OF COMPOUND AS HYPOXIA MIMETICS, AND USES THEREOF

(75) Inventors: Xinshan Kang, Fujian (CN); Wei Long, Beijing (CN); Fei Wang, Beijing (CN); Cunbo Ma, Beijing (CN); Liufeng Zhou, Beijing (CN); Yunyan Hu, Beijing (CN); Yanping Wang, Beijing (CN); Hong Cao, Beijing (CN); Yinxiang Wang, Beijing (CN); Fenlai Tan, Beijing (CN)

(73) Assignee: BEIJING BETTA PHARMACEUTICALS CO., LTD, Beijing (CN)

( * ) Notice: Subject to any disclaimer, the term of this patent is extended or adjusted under 35 U.S.C. 154(b) by 0 days.

(21) Appl. No.: 14/166,203

(22) PCT Filed: Jul. 30, 2012

(86) PCT No.: PCT/CN2012/079361
§ 371 (c)(1),
(2), (4) Date: Jan. 28, 2014

(87) PCT Pub. No.: WO2013/017063
PCT Pub. Date: Feb. 7, 2013

(65) Prior Publication Data
US 2014/0343137 A1    Nov. 20, 2014

(30) Foreign Application Priority Data

Jul. 29, 2011 (CN) ............. 2011 1 0215826
Aug. 2, 2011 (CN) ............. 2011 1 0219607
Aug. 15, 2011 (CN) ............. 2011 1 0232754

(51) Int. Cl.
*A01N 43/16* (2006.01)
*C07D 311/56* (2006.01)

(52) U.S. Cl.
CPC ................. *C07D 311/56* (2013.01)

(58) Field of Classification Search
CPC ... A61K 31/37; A61K 31/352; C07D 311/16; C07D 311/56; A01N 43/16
USPC ........................................ 514/457; 549/285
See application file for complete search history.

(56) References Cited

FOREIGN PATENT DOCUMENTS

WO    WO 2009100250 A1 *  8/2009
WO    WO 2011006355 A1 *  1/2011 ............. A61K 31/37

* cited by examiner

*Primary Examiner* — Nyeemah A Grazier
*Assistant Examiner* — Sager Patel
(74) *Attorney, Agent, or Firm* — Weisun Rao; Greenberg Traurig, LLP (57) ABSTRACT

The polymorphic forms of the compound of Formula I, the preparation thereof including the preparation of the intermediates, the pharmaceutical compositions thereof and the uses of a polymorph above in the manufacture of medicaments for treating a disease, a disorder or a condition are disclosed.

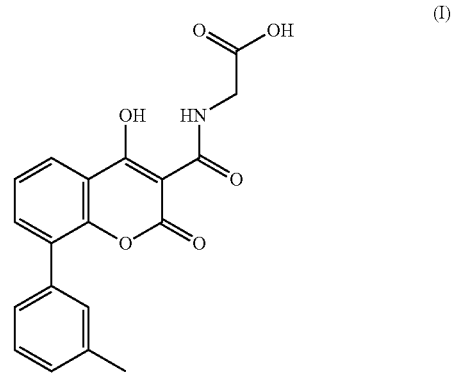

9 Claims, 5 Drawing Sheets

STABLE POLYMORPHIC FORMS OF COMPOUND AS HYPOXIA MIMETICS, AND USES THEREOF

FIELD OF THE INVENTION

The present invention relates to the polymorphic forms of a novel compound, and their use in inhibiting prolyl hydroxylase activity. The present invention also relates to a method of using at least one of the polymorphs thereof in modulating HIF level or activity, treating a disease, a disorder or a condition associated with increasing or lowing HIF level or activity, in a subject

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an heterodimer (HIFαβ):HIF is a constitutive nuclear protein that dimerizes with oxygen-regulated HIF subunits. Oxygen regulation occurs through hydroxylation of the HIF subunits, which are then rapidly destroyed by the proteasome. In oxygenated cells, the von Hippel-Lindau tumor suppressor protein (pVHL) binds to hydroxylated HIF-subunits, thereby promoting their ubiquitin dependent proteolysis. This process is suppressed under hypoxic conditions, stabilizing HIF and promoting transcriptional activation by the HIF complex.

Hydroxylation of HIF-subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1, as well as Factor Inhibiting HIF (FIH), which hydroxylates Asn 803 of human HIF1. Inhibition of FIH or the PHDs leads to HIF stabilization and transcriptional activation.

Inhibition of PHDs also leads to HIF stabilization and promoting transcriptional activation by the HIF complex, which may in turn provide a potential treatment for ischemia or anemia. There have been multiple patents that cover the chemical structure designs of the potential PHDs inhibitors, see, e.g., WO2004108681, WO2007070359 and WO2011006355.

DESCRIPTION OF THE INVENTION

The present invention relates to approximately pure crystalline polymorphs, wherein these polymorphs are the polymorphs of the compound of Formula I, Formula I The compound of Formula I of the present invention can exist in one or more crystal forms.

The present invention provides a crystalline polymorph of the compound of Formula I, N-[(4-hydroxy-2-oxo-8-(3-methyl-phenyl)-2H-3-coloralkenyl)carbonyl]glycine.

The present invention provides a preferable crystalline polymorph Crystalline Form I that exhibits an X-ray powder diffraction pattern having characteristic peaks at diffraction angles 2θ of 7.1°, 12.4° and 20.2°.

The present invention further provides preferred embodiments of the Crystalline Form I.

Preferably, the X-ray powder diffraction pattern has characteristic peaks, expressed in terms of the interplanar distance of 12.4 Å, 7.2 Å and 4.4 Å.

Preferably, the X-ray powder diffraction pattern has characteristic peaks at diffraction angles 2θ of 7.1°, 10.4°, 12.4°, 17.0° and 20.2°.

Preferably, the X-ray powder diffraction pattern has characteristic peaks, expressed in terms of the interplanar distance of 12.4 Å, 8.5 Å, 7.2 Å, 5.2 Å and 4.4 Å.

Preferably, the X-ray powder diffraction pattern has characteristic peaks at diffraction angles 2θ of 7.1°, 8.4°, 10.4°, 12.4°, 13.3°, 17.0°, 20.2° and 27.6°.

Preferably, the X-ray powder diffraction pattern has characteristic peaks, expressed in terms of the interplanar distance of 12.4 Å, 10.6 Å, 8.5 Å, 7.2 Å, 6.7 Å, 5.2 Å, 4.4 Å and 3.2 Å.

Figure 1:
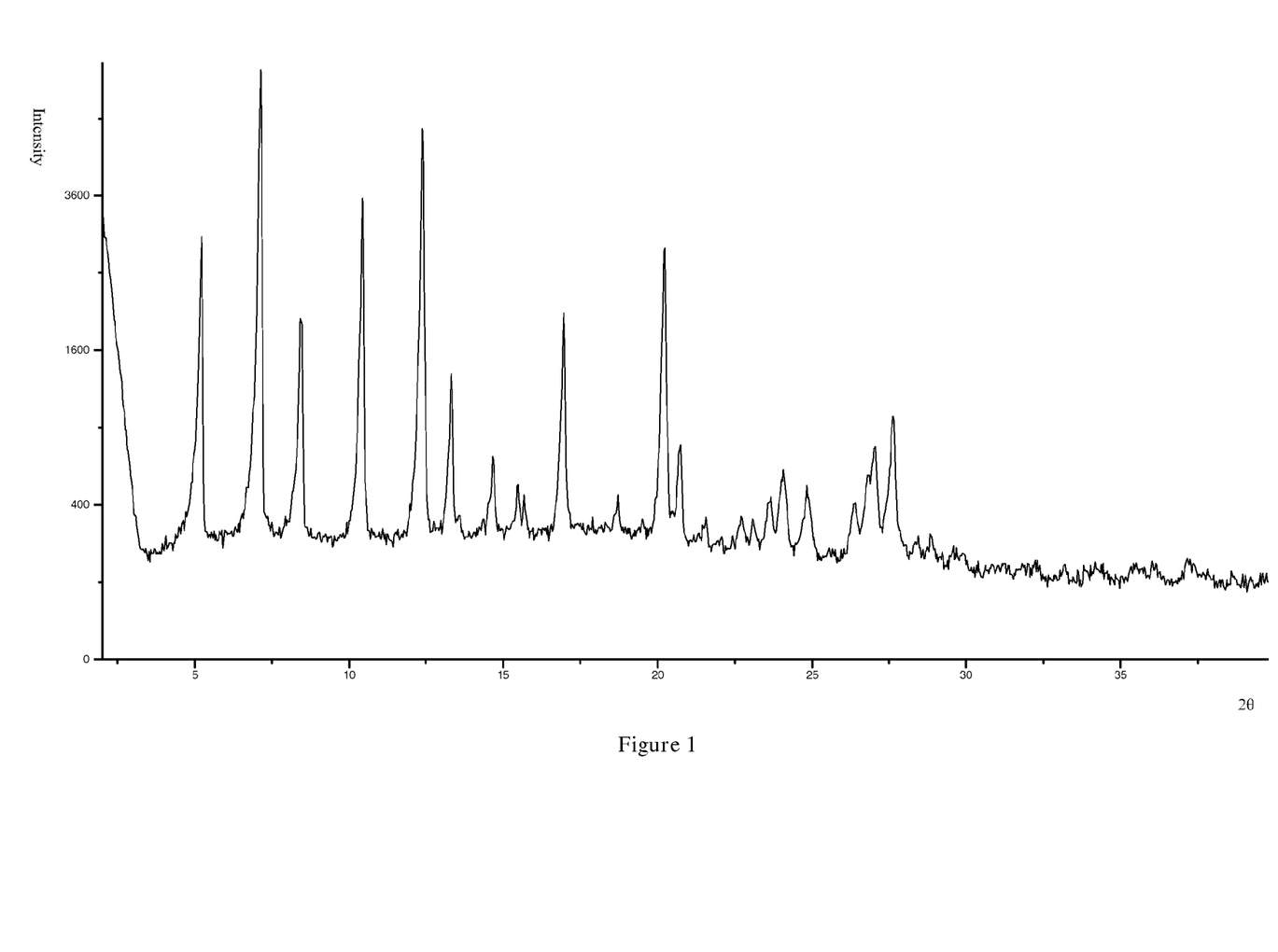
FIG. 1 shows the X-ray powder diffraction pattern of Crystalline Form I of the compound of Formula I

Preferably, the X-ray powder diffraction pattern of the Crystalline Form I is shown as in FIG. 1.

The X-ray diffraction pattern depicted in FIG. 1 is summarized in Table A.

TABLE A

| 2θ (2 theta) ± 0.2 (degrees) | d-spacing ± 0.2 [Å] |
|---|---|
| 7.1 | 12.4 |
| 8.4 | 10.6 |
| 10.4 | 8.5 |
| 12.4 | 7.2 |
| 13.3 | 6.7 |
| 17.0 | 5.2 |
| 20.2 | 4.4 |
| 27.6 | 3.2 |

Preferably, the Crystalline Form I has a melting point of 190-193° C.

Preferably, the Crystalline Form I has a purity of ≥85%.

Preferably, the Crystalline Form I has a purity of ≥95%.

Preferably, the Crystalline Form I has a purity of ≥99%.

The present invention further provides a method of preparing Crystalline Form I form, comprising the steps of:

dissolving the compound of Formula I in a solvent at room temperature, followed by a spontaneous precipitation, and recovering the resulted crystalline polymorph, wherein the solvent is selected from acetone, ethyl acetate, isopropanol, or the mixed solvent of acetone/methanol, acetone/heptane, acetone/isopropanol, acetone/IPAc, THF/methanol, THF/EtOAc, THF/heptane, THF/acetonitrile, THF/isopropanol, THF/MTBE or THF/CH$_2$Cl$_2$;

or, slurrying excess amount of the compound of Formula I in CH$_2$Cl$_2$ or the mixed solvent of H$_2$O/THF or H$_2$O/acetone for at least 48 hrs. at room temperature, or in heptane, methanol or the mixed solvent of H$_2$O/THF for at least 48 hr at 50° C., and recovering the resulted crystalline polymorph.

The present invention provides a preferable crystalline polymorph Crystalline Form II that exhibits an X-ray powder diffraction pattern having characteristic peaks at diffraction angles 2θ of 6.5°, 11.2° and 18.4°.

The present invention further provides preferred embodiments of the Crystalline Form II.

Preferably, the X-ray powder diffraction pattern has characteristic peaks, expressed in terms of the interplanar distance of 13.6 Å, 7.9 Å and 4.8 Å.

Preferably, the X-ray powder diffraction pattern has characteristic peaks at diffraction angles 2θ of 6.5°, 9.3°, 11.2°, 15.4° and 18.4°.

Preferably, the X-ray powder diffraction pattern has characteristic peaks, expressed in terms of the interplanar distance of 13.6 Å, 9.5 Å, 7.9 Å, 5.8 Å and 4.8 Å.

Preferably, the X-ray powder diffraction pattern has characteristic peaks at diffraction angles 2θ of 6.5°, 9.3°, 11.2°, 13.0°, 14.1°, 15.4° 18.4° and 24.6°.

Preferably, the X-ray powder diffraction pattern has characteristic peaks, expressed in terms of the interplanar distance of 13.6 Å, 9.5 Å, 7.9 Å, 6.8 Å, 6.3 Å, 5.8 Å, 4.8 Å and 3.6 Å.

Figure 2:
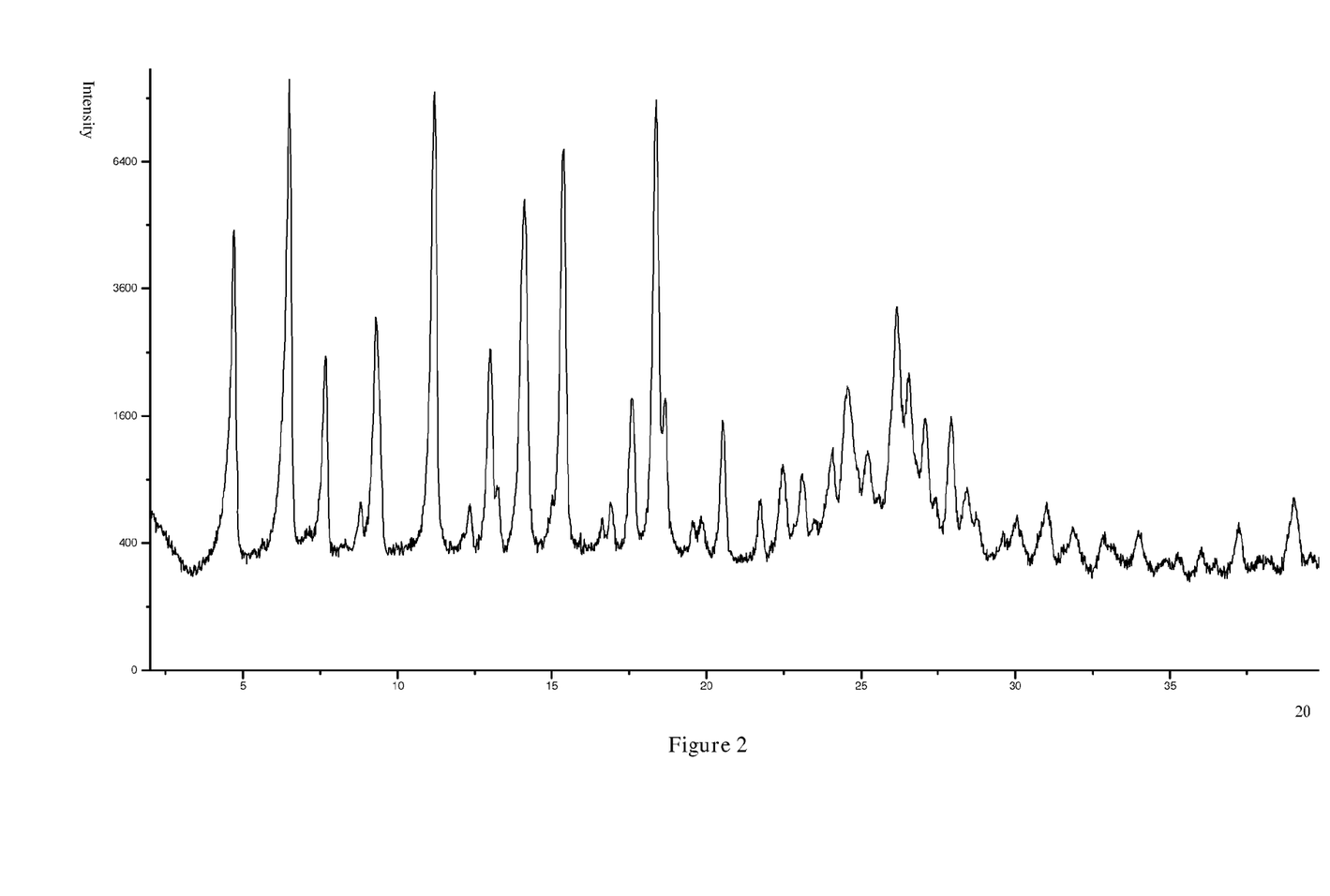
FIG. 2 shows the X-ray powder diffraction pattern of Crystalline Form II of the compound of Formula I

Preferably, the X-ray powder diffraction pattern of crystalline polymorph Crystalline Form II is shown as in FIG. 2.

The X-ray diffraction pattern depicted in FIG. 2 is summarized in Table B.

TABLE B

| 2θ (2 theta) ± 0.2 (degrees) | d-spacing ± 0.2 [Å] |
| --- | --- |
| 6.5 | 13.6 |
| 9.3 | 9.5 |
| 11.2 | 7.9 |
| 13.0 | 6.8 |
| 14.1 | 6.3 |
| 15.4 | 5.8 |
| 18.4 | 4.8 |
| 24.6 | 3.6 |

Preferably, the Crystalline Form II has a melting point of 129-132° C.

Preferably, the Crystalline Form II has a purity of ≥85%.
Preferably, the Crystalline Form II has a purity of ≥95%.
Preferably, the Crystalline Form II has a purity of ≥99%.

The present invention also provides a method of preparing the Crystalline Form II comprising the steps of dissolving the compound of Formula I in a solvent, followed by a spontaneous precipitation, and recovering the resulted crystalline polymorph, wherein the solvent is selected from dimethylformamide or the mixed solvent of THF/dimethylformamide.

The present invention further provides a preferable crystalline polymorph Crystalline Form III of the compound of Formula I that exhibits an X-ray powder diffraction pattern having characteristic peaks at diffraction angles 2θ of 12.3°, 16.6° and 25.4°.

The present invention further provides preferred embodiments of the Crystalline Form III.

Preferably, the X-ray powder diffraction pattern has characteristic peaks, expressed in terms of the interplanar distance of 7.2 Å, 5.3 Å and 3.5 Å.

Preferably, the X-ray powder diffraction pattern has characteristic peaks at diffraction angles 2θ of 12.3°, 16.6°, 21.8°, 25.4° and 29.2°.

Preferably, the X-ray powder diffraction pattern has characteristic peaks, expressed in terms of the interplanar distance of 7.2 Å, 5.3 Å, 4.1 Å, 3.5 Å and 3.1 Å.

Preferably, the X-ray powder diffraction pattern has characteristic peaks at diffraction angles 2θ of 12.3°, 13.0°, 16.6°, 18.6°, 21.8°, 25.4°, 26.9° and 29.2°.

Preferably, the X-ray powder diffraction pattern has characteristic peaks, expressed in terms of the interplanar distance of 7.2 Å, 6.8 Å, 5.3 Å, 4.8 Å, 4.1 Å, 3.5 Å, 3.3 Å and 3.1 Å.

Figure 3:
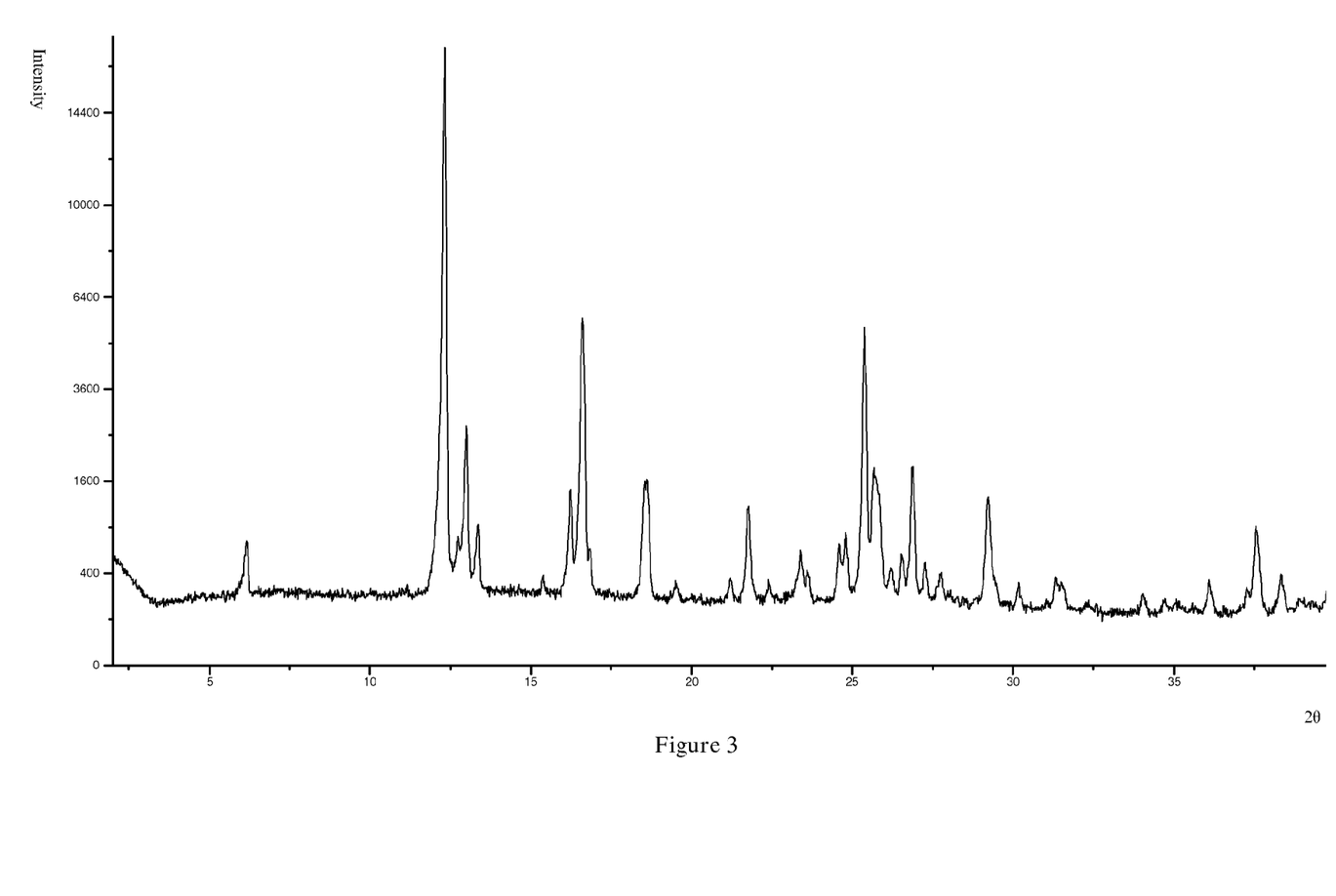
FIG. 3 shows the X-ray powder diffraction pattern of Crystalline Form III of the compound of Formula I

Preferably, the X-ray powder diffraction pattern of the Crystalline Form III is shown as in FIG. 3.

The X-ray diffraction pattern depicted in FIG. 3 is summarized in Table C.

TABLE C

| 2θ (2 theta) ± 0.2 (degrees) | d-spacing ± 0.2 [Å] |
| --- | --- |
| 12.3 | 7.2 |
| 13.0 | 6.8 |
| 16.6 | 5.3 |
| 18.6 | 4.8 |
| 21.8 | 4.1 |
| 25.4 | 3.5 |
| 26.9 | 3.3 |
| 29.2 | 3.1 |

Preferably, the Crystalline Form III has a melting point of 196-199° C.

Preferably, the Crystalline Form III has a purity of ≥85%.
Preferably, the Crystalline Form III has a purity of ≥95%.
Preferably, the Crystalline Form III has a purity of ≥99%.

The present invention also provides a method of preparing the Crystalline Form III, comprising the steps of:

dissolving the compound of Formula I in isopropyl acetate (IPAc), followed by a spontaneous precipitation, and recovering the resulted crystalline polymorph;

or, slurrying excess amount of the Compound of Formula I in a solvent selected from methyl tert-butyl ether (MTBE), IPAc or EtOAc, for at least 48 hr, and recovering the resulted crystalline polymorph, wherein the temperature of slurrying is preferably 20° C.-50° C.;

or, slurrying excess amount of the compound of Formula I in the mixed solvent of acetone/H$_2$O for at least 48 hrs. at room temperature, or in the mixed solvent of EtOAc/THF at 50° C. for at least 48 hrs., and recovering the resulted crystalline polymorph, wherein the volume ratio of EtOAc/THF is 3:1, and the volume ratio of acetone/H$_2$O is 1:1;

or, heating the compound of Formula I to 195° C. under inert gas, and then cooling down to room temperature, and recovering the resulted crystalline polymorph;

or, dissolving the compound of Formula I in a solvent, adding the Crystalline Form III as crystal seed, followed by a spontaneous precipitation, and recovering the resulted crystalline polymorph, wherein the solvent includes, but is not limited to, MTBE, IPAc or EtOAc;

or, dissolving the compound of Formula I in a mixed solvent, adding the Crystalline Form III as crystal seed, followed by a spontaneous precipitation, and recovering the resulted crystalline polymorph, wherein the mixed solvent includes, but is not limited to, a mixed solvent including EtOAc, THF, acetone or water, preferably, a mixed solvent of EtOAc/THF or acetone/$H_2O$;

or, heating and dissolving the compound of Formula I in a solvent to from a solution, cooling while adding the Crystalline Form III as crystal seed, and recovering the resulted crystalline polymorph, wherein the solvent includes, but is not limited to, isopropanol (IPA), 4-methyl-2-pentanone, propyl acetate, MTBE, IPAc or EtOAc;

or, heating and dissolving the compound of Formula I in a mixed solvent to from a solution, adding the Crystalline Form III as crystal seed, cooling, crystallizing, and recovering the resulted crystalline polymorph, wherein the mixed solvent includes, but is not limited to, a mixed solvent containing EtOAc, THF, acetone or water, preferably, a mixed solvent of IPA/$H_2O$, EtOAc/THF, IPAc/THF, MTBE/THF or acetone/$H_2O$.

The present invention further provides a preferable crystalline polymorph Crystalline Form IV of the compound of Formula I that exhibits an X-ray powder diffraction pattern having characteristic peaks at diffraction angles 2θ of 12.5°, 17.0° and 22.3°.

The present invention further provides preferred embodiments of the Crystalline Form IV.

Preferably, the X-ray powder diffraction pattern has characteristic peaks, expressed in terms of the interplanar distance of 7.1 Å, 5.2 Å and 4.0 Å.

Preferably, the X-ray powder diffraction pattern has characteristic peaks at diffraction angles 2θ of 8.4°, 12.5°, 17.0°, 18.1° and 22.3°.

Preferably, the X-ray powder diffraction pattern has characteristic peaks, expressed in terms of the interplanar distance of 10.5 Å, 7.1 Å, 5.2 Å, 4.9 Å and 4.0 Å.

Preferably, the X-ray powder diffraction pattern has characteristic peaks at diffraction angles 2θ of 8.4°, 9.0°, 11.3°, 12.5°, 17.0°, 18.1°, 22.3° and 28.2°.

Preferably, the X-ray powder diffraction pattern has characteristic peaks, expressed in terms of the interplanar distance of 10.5 Å, 9.8 Å, 7.9 Å, 7.1 Å, 5.2 Å, 4.9 Å, 4.0 Å and 3.2 Å.

Figure 4:
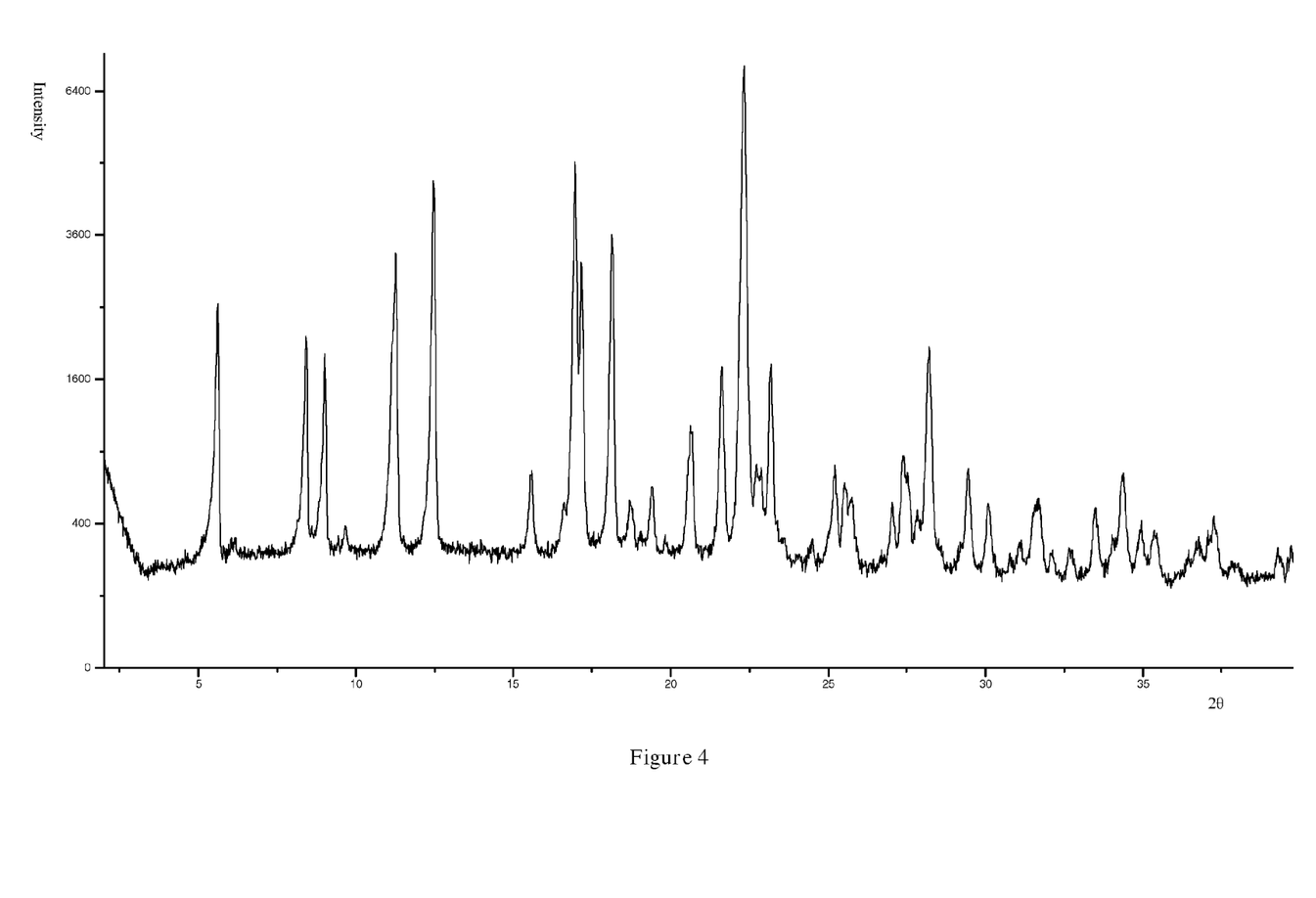
FIG. 4 shows the X-ray powder diffraction pattern of Crystalline Form IV of the compound of Formula I

Preferably, the X-ray powder diffraction pattern of the Crystalline Form IV is shown as in FIG. 4.

The X-ray diffraction pattern depicted in FIG. 4 is summarized in Table D.

TABLE D

| 2θ (2 theta) ± 0.2 (degrees) | d-spacing ± 0.2 [Å] |
|---|---|
| 8.4 | 10.5 |
| 9.0 | 9.8 |
| 11.3 | 7.9 |
| 12.5 | 7.1 |
| 17.0 | 5.2 |
| 18.1 | 4.9 |
| 22.3 | 4.0 |
| 28.2 | 3.2 |

Preferably, the Crystalline Form IV has a melting point of 189-193° C.

Preferably, the Crystalline Form IV has a purity of ≥85%.
Preferably, the Crystalline Form IV has a purity of ≥95%.
Preferably, the Crystalline Form IV has a purity of ≥99%.

The present invention also provides a method of preparing the Crystalline Form IV, comprising the steps of:

heating the Crystalline Form I to 50° C., and then cooling down to room temperature, and recovering the resulted crystalline polymorph;

or, dissolving the compound of Formula I in THF, followed by a spontaneous precipitation, and recovering the resulted crystalline polymorph.

The present invention provides a preferable crystalline polymorph Crystalline Form V that exhibits an X-ray powder diffraction pattern having characteristic peaks at diffraction angles 2θ of 12.3°, 21.8° and 27.6°.

The present invention further provides preferred embodiments of the Crystalline Form V.

Preferably, the X-ray powder diffraction pattern has characteristic peaks, expressed in terms of the interplanar distance of 7.2 Å, 4.1 Å and 3.2 Å.

Preferably, the X-ray powder diffraction pattern has characteristic peaks at diffraction angles 2θ of 12.3°, 16.8°, 17.9°, 21.8° and 27.6°.

Preferably, the X-ray powder diffraction pattern has characteristic peaks, expressed in terms of the interplanar distance of 7.2 Å, 5.3 Å, 5.0 Å, 4.1 Å and 3.2 Å.

Preferably, the X-ray powder diffraction pattern has characteristic peaks at diffraction angles 2θ of 11.1°, 12.3°, 16.8°, 17.9°, 21.2°, 21.8°, 23.0° and 27.6°.

Preferably, the X-ray powder diffraction pattern has characteristic peaks, expressed in terms of the interplanar distance of 8.0 Å, 7.2 Å, 5.3 Å, 5.0 Å, 4.2 Å, 4.1 Å, 3.9 Å and 3.2 Å.

Figure 5:
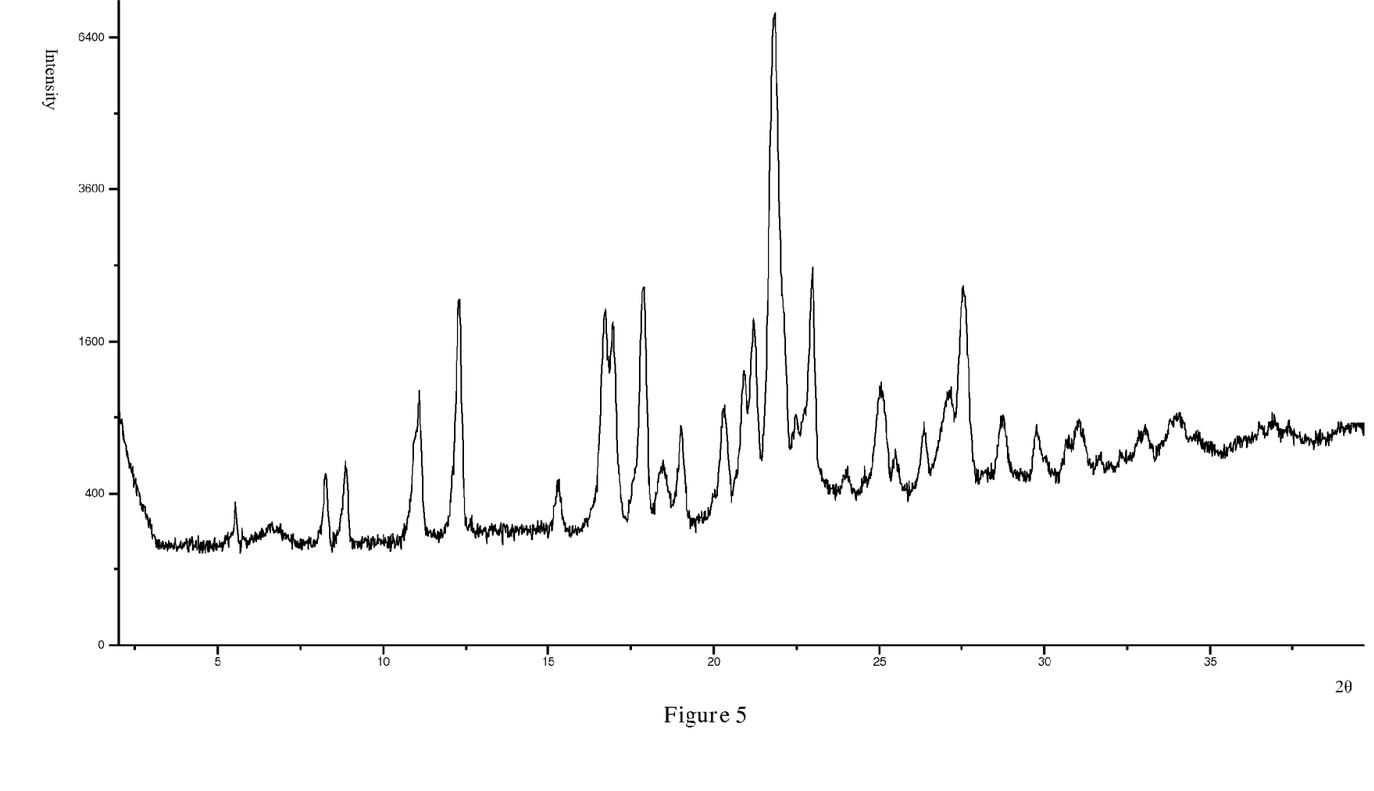
FIG. 5 shows the X-ray powder diffraction pattern of Crystalline Form V of the compound of Formula I

Preferably, the X-ray powder diffraction pattern of the Crystalline Form V is shown as in FIG. 5.

The X-ray diffraction pattern depicted in FIG. 5 is summarized in Table E.

TABLE E

| 2θ (2 theta) ± 0.2 (degrees) | d-spacing ± 0.2 [Å] |
|---|---|
| 11.1 | 8.0 |
| 12.3 | 7.2 |
| 16.8 | 5.3 |
| 17.9 | 5.0 |
| 21.2 | 4.2 |
| 21.8 | 4.1 |
| 23.0 | 3.9 |
| 27.6 | 3.2 |

Preferably, the Crystalline Form V has a melting point of 192-195° C.

Preferably, the Crystalline Form V has a purity of ≥85%.
Preferably, the Crystalline Form V has a purity of ≥95%.
Preferably, the Crystalline Form V has a purity of ≥99%.

The present invention also provides a method of preparing the Crystalline Form V, comprising the steps of heating the Crystalline Form IV to 175° C. under inert gas, and recovering the resulted crystalline polymorph.

The present invention also provides a method of preparing the compound of Formula I comprising the steps of:

(a) Synthesis of Compound 2

Compound 1 was dissolved in acetic acid, stirred and heated to 75° C.-85° C. Liquid bromine was slowly added in drop-wise and reacted for 7-9 hrs. till reaction completion verified by TLC. Cooled down to room temperature. The reaction solution was poured into 4000 mL of saturated sodium bisulfite (NaHSO$_3$) solution. The resulted precipitate was filtered and washed with water, and dried in vacuum below 60° C. to obtain Compound 2;

(b) Synthesis of Compound 3

In inert gas, Compound 2, 4-methylphenylboronic acid, Pd(PPh$_3$)$_4$, N,N-dimethylformamide and Na$_2$CO$_3$ aqueous solution were mixed, reacted at 75° C.-85° C. for 10-14 hrs. The reaction solution was cooled down to room temperature after the reaction completion verified by TLC. Water and ethyl acetate were added. The water phase was further extracted with ethyl acetate three times. The organic phase was combined, washed with saturated brine twice, dried by anhydrous sodium sulfate (Na$_2$SO$_4$), and distilled in vacuum to remove ethyl acetate, resulted in a crude product. The crude product was recrystallized in methanol to obtain Compound 3;

(c) Synthesis of Compound 4

Compound 3 was added into water. Ammonium formate and Pd/C (5%) were then added and refluxed for about 1.5-2.5 hrs. After cooling down and removing Pd/C, the reaction mixture was extracted with ethyl acetate twice. The organic phase was combined, washed with water and saturated brines, dried by anhydrous sodium sulfate (Na$_2$SO$_4$), filtered, and distilled in vacuum to remove the solvent, to obtain Compound 4;

(d) Synthesis of Compound 5

Compound 4, acetic anhydride and phosphoric acid were reacted at 45° C.-55° C. till completion, then cooled down to room temperature. Water was added and stirred at 45° C.-55° C. till hydrolization was complete. The reaction mixture was cooled down and filtered. The resulted solid was dried to obtain Compound 5;

(e) Synthesis of Compound 6

Compound 5 and 1-hydroxy benzotriazole (HOBt) were dissolved in THF and cooled down to below 0° C. Dicyclohexylcarbodiimide (DCC) was added in multiple batches and stirred at below 10° C. for 10-14 hrs., and filtered to retain the filtrate. dimethyl malonate was dissolved in THF. NaH (70% oil dispersion) was added first, followed by the filtrate obtained above while stirring, and the mixture was reacted for 1-3 hrs. THF was removed by vacuum distillation. Methanol and 10% HCl were then added and stirred overnight at room temperature. The precipitate was filtered and washed with methanol to obtain Compound 6;

(f) Synthesis of Compound 7

Tert-butyl glycinate hydrochloride and sodium methoxide were added into methanol and stirred, followed by distillation to remove methanol. THF and Compound 6 were added, and reacted overnight at 55° C.-65° C.

The reaction mixture was distilled in vacuum to remove THF. Methanol was then added and stirred for 1.5-2.5 hrs., and filtered to obtain Compound 7;

(g) Synthesis of Compound 8, the Compound of Formula I

Compound 7, $CH_2Cl_2$ and trifluoroacetic acid (TFA) was mixed, stirred and reacted for 3.5-4.5 hrs. $CH_2Cl_2$ and TFA was removed by distillation, and the residue was recrystallized in methanol to obtain Compound 8.

The present invention further provides a composition comprising effective amount of any one of crystalline polymorph mentioned above, and a pharmaceutically acceptable excipient, adjuvant or carrier.

The present invention also provides preferable embodiments of the pharmaceutical composition.

Preferably, the pharmaceutical composition comprises a therapeutically effective amount of crystalline polymorph of the present invention, in combination with at least one of additional active ingredient.

Preferably, the pharmaceutical composition is used in an oral administration.

Preferably, the pharmaceutical composition is used in a tablet or a capsule.

Preferably, the pharmaceutical composition comprises 1 wt %-99 wt % of the crystalline polymorph of the present invention.

Preferably, the pharmaceutical composition comprises 1 wt %-70 wt % of the crystalline polymorph of the present invention.

Preferably, the pharmaceutical composition comprises 10 wt %-30 wt % of the crystalline polymorph of the present invention.

The present invention also provides a use of any one of the crystalline polymorph mentioned above in the manufacturing a medicament for regulating HIF level or HIF activity.

The present invention also provides preferable embodiments of the uses of the crystalline polymorphs.

Preferably, the crystalline polymorphs of the present invention can be used in manufacturing a medicament for the treatment of a disease, disorder, or condition associated with HIF level or HIF activity.

Preferably, the crystalline polymorphs of the present invention can be used in manufacturing a medicament for the treatment of ischemia, anemia, or a disease, disorder or condition associated with ischemia or anemia.

Preferably, the crystalline polymorphs of the present invention can be used in manufacturing a medicament for the treatment of a disease, disorder, or condition selected from ischemia, anemia, wound healing, auto-transplantation, allo-transplantation, xeno-transplantation, systemic high blood pressure, thalassemia, diabetes, cancer or an inflammatory disorder, or a combination of two or more thereof, in a subject.

Also provided is a method of modulating HIF levels or activity in a subject by administering to the subject one crystalline polymorph of the present invention.

Further provided is a method for treating a disease, a disorder, or a condition associated with HIF level or HIF activity in a subject by administering to the subject one crystalline polymorph of the present invention.

Additionally provided is a method for treating ischemia, anemia, or a disease, a disorder or a condition associated with ischemia or anemia in a subject by administering to the subject one crystalline polymorph of the present invention.

Yet additionally provided is a method for treating a disease, a disorder, or a condition selected from ischemia, anemia, wound healing, auto-transplantation, allo-transplantation, xeno-transplantation, systemic high blood pressure, thalassemia, diabetes, cancer or an inflammatory disorder, or a combination of two or more thereof, in a subject by administering to the subject one crystalline polymorph of the present invention.

All the crystalline polymorphs of the present invention are approximately pure.

The term "approximately pure" as herein used refers to at least 85 wt %, preferably at least wt %, more preferably at least 99 wt % of the compound of Formula I, N-[(4-hydroxy-2-oxo-8-(3-methyl-phenyl)-2H-3-coloralkenyl)carbonyl] glycine, of the present invention is a crystal from, particularly in the crystal forms of present invention.

The main peaks described in the crystalline polymorphs above are reproducible and are within the error limit (the specified value ±0.2).

In the present invention, "the X-ray powder diffraction pattern shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 2, 3, 4 or 5 refers to the X-ray powder diffraction pattern that show major peaks as in FIG. 2, 3, 4 or 5, wherein major peaks refer to those with the relative intensity greater than 10%, preferably greater than 30%, relative to the highest peak (with its relative intensity designated to be 100%) in FIG. 2, 3, 4 or 5, respectively.

Crystallization also can be achieved by using or not using a crystal seed that is suitable for crystallizing the compound of the present invention.

Crystallization in the present invention is related to dynamics and equilibria among different crystal forms under certain conditions. Therefore, those skilled in the art will realize that the resulting crystal form depends on the kinetics and thermodynamics of the crystallization process.

Under certain conditions (solvent system, temperature, pressure, and the concentration of the compound of the present invention), a crystal form may be more stable than another one (or, actually be more stable than any other crystal forms). However, the polymorphs that are less stable thermodynamically may be favorable in kinetics. The crystalline form may also be affected by factors other than kinetics, such as time, impurity distribution, agitation, presence or absence of crystal seed.

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/ or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combined active ingredient for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as a tablet, powder, granule, a capsule and the like, a liquid preparation such as water or oil suspension or other liquid preparation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a unit dose of single unit administration with an accurate dosage. In addition, the pharmaceutical composition may further comprise additional active ingredients.

All formulations of the pharmaceutical composition of the present invention can be produced by the conventional methods in the pharmaceutical field. For example, one can mix the active ingredient with one or more excipients, and make the mixture into the target formulation.

The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc; a binder such as cellulose derivatives, alginates, gelatin and polyvinylpyrrolidone; a wetting agent such as glycerol; a disintegrating agent such as agar, calcium carbonate and sodium bicarbonate; an absorption enhancer such as quaternary ammoniums; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a diffusion enhancer, a polymer, a fragrance, a sweetener, and a dye. Preferably, the excipient is suitable for desired formulation and administration type.

The term "disease" or "disorder" refers to any disease, discomfort, illness, symptoms or indications.

The X-ray powder diffraction (XRPD) patterns shown as in FIGS. 1, 2, 3, 4 and 5 were generated on a PANalytical X-ray Diffraction System with Empyrean console. The diffraction peak positions were calibrated by single crystal silicon which has a 2-theta (2θ) value of 28.443 degree. An Empyrean Cu LEF X-ray tube K-Alpha radiation was used as the source.

EXAMPLES

The present invention is further exemplified, but not limited, by the following examples that illustrate the invention. In the examples of the present invention, the techniques or methods, unless expressly stated otherwise, are conventional techniques or methods in the art.

Example 1

Synthesis of N-[(4-hydroxy-2-oxo-8-(3-methyl-phenyl)-2H-3-coloralkenyl) carbonyl]glycine—Compound 8 (the compound of Formula I)

(a) Synthesis of Compound 2

Compound 1 (200 g) was dissolved in 3000 mL of acetic acid in a 5 L of three-necked flask, and stirred and heated to 80° C. Liquid bromine was slowly added in drop-wise and reacted for 8 hrs. till reaction completion verified by TLC. Cooled down to room temperature. The reaction solution was poured into 4000 mL of saturated sodium bisulfite ($NaHSO_3$) solution. The resulted precipitate was filtered and washed with water, and dried in vacuum below 60° C. to obtain 204.6 g of white solid (Compound 2), with the purity of greater than 98%.

(b) Synthesis of Compound 3

Under inert gas ($N_2$), 15 g of 3-bromo-5-chloro salicylic acid (Compound 2), 8.16 g of 4-methylphenylboronic acid, 2 g of Pd(PPh$_3$)$_4$, 120 mL of N,N-dimethylformamide and 30 mL of 2 mol/L $Na_2CO_3$ aqueous solution were mixed, heated to 80° C. and reacted for 12 hrs. The reaction solution was cooled down to room temperature after the reaction completed verified by TLC, and 500 mL of water and 300 mL of ethyl acetate were added. The water phase was further extracted with 200 ml ethyl acetate three times. The organic phase was combined, washed with 300 ml saturated brine twice, dried by anhydrous sodium sulfate ($Na_2SO_4$), and distilled in vacuum to remove ethyl acetate, resulted in 21.6 g of crude product. The crude product was recrystallized in methanol to obtain 18.2 g of Compound 3.

(c) Synthesis of Compound 4

Compound 3 (27 g) was added into 250 mL of water. 5 g of ammonium formate and 8.7 g of Pd/C (5%) were then added and refluxed for about 2 hrs. After cooling down and removing Pd/C, the reaction mixture was extracted with 100 mL of ethyl acetate twice. The organic phase was combined, washed with water and saturated brines, dried by anhydrous sodium sulfate ($Na_2SO_4$), filtered, and distilled in vacuum to remove the solvent, to obtain Compound 4.

(d) Synthesis of Compound 5

The mixture of Compound 4 (27 g), acetic anhydride (130 mL) and phosphoric acid (1 mL) was reacted at 50° C. until the reaction was completed. The reaction solution was cooled down to room temperature, subject to adding 500 mL of water, stirring, and completely hydrolyzing at 50° C. And the solution was cooled down to 0° C. to precipitate a solid, and the solid was dried, to obtain 24.4 g of Compound 5.

(e) Synthesis of Compound 6

13 g of Compound 5 and 6.8 g of 1-hydroxy benzotriazole (HOBt) were dissolved in THF and cooled down to below 0° C. 10.4 g of dicyclohexylcarbodiimide (DCC) was added in multiple batches and stirred at below 10° C. for about 12 hrs., and filtered to retain the filtrate.

6.6 g of dimethyl malonate was dissolved in 400 mL of THF. 3.8 g of NaH (70% oil dispersion) was added first, followed by the filtrate obtained above while stirring, and the mixture was reacted for 2 hrs. THF was removed by vacuum distillation. 200 mL of methanol and 200 mL of 10% HCl were then added and stirred overnight at room temperature. The precipitate was filtered and washed with 200 mL of methanol to obtain 6 g of Compound 6.

(f) Synthesis of Compound 7

Tert-butyl glycinate hydrochloride (13.5 g) and sodium methoxide (4.4 g) were added into 200 mL of methanol and stirred, followed by distillation to remove methanol. 200 mL of THF and Compound 6 (6.0 g) were added, and reacted overnight at 60° C.

The reaction mixture was distilled in vacuum to remove THF. 400 mL of methanol was then added and stirred for 2 hrs., and filtered to obtain 3.5 g of white solid (Compound 7).

(g) Synthesis of Compound 8

Compound 7 (0.5 g), 5 mL of $CH_2Cl_2$ and trifluoroacetic acid (5 mL) were added into a 100 mL of three-necked flask, stirred and reacted for about 4 hrs. The reaction mixture was distilled to remove $CH_2Cl_2$ and trifluoroacetic acid, and the residue was recrystallized in methanol to obtain Compound 8 (the compound of Formula I).

Example 2

Preparation of Crystalline Form I

The compound of Formula I prepared from Example 1 was dissolved in acetone, ethyl acetate (EtOAc), isopropanol, methyl tert-butyl ether (MTBE), or the mixed solvent of acetone/methanol, acetone/heptane, acetone/isopropanol, acetone/isopropyl acetate (IPAc), THF/methanol, THF/EtOAc, THF/heptane, THF/acetonitrile, THF/isopropanol, THF/MTBE or THF/CH$_2$Cl$_2$, followed by a spontaneous precipitation to obtain the desired Crystalline Form I, with the melting point of 190-193° C.

Example 3

Preparation of Crystalline Form I

A slurry suspension of excess amount of the compound of Formula I prepared as in Example 1, was stirred in dichloromethane (CH$_2$Cl$_2$) or the mixed solvent of H$_2$O/THF or H$_2$O/acetone at room temperature for at least 48 hrs., to obtain the desired Crystalline Form I.

Example 4

Preparation of Crystalline Form I

A slurry suspension of excess amount of the compound of Formula I prepared as in Example 1, was stirred in heptane, methanol, or the mixed solvent of H$_2$O/THF at 50° C. for 48 hrs. or 72 hrs., to obtain the desired Crystalline Form I.

Example 5

Preparation of Crystalline Form II

The compound of Formula I prepared as in Example 1 was dissolved in the mixed solvent of THF/dimethylformamide or dimethylformamide, followed by a spontaneous precipitation to obtain the desired Crystalline Form II, with the melting point of 129-132° C.

Example 6

Preparation of Crystalline Form III

The compound of Formula I prepared as in Example 1 was dissolved in IPAc, followed by a spontaneous precipitation to obtain the desired Crystalline Form III, with the melting point of 196-199° C.

Example 7

Preparation of Crystalline Form III

A slurry suspension of excess amount of the compound of Formula I prepared as in Example 1, was stirred in MTBE, IPAc or EtOAc at room temperature for at least 48 hrs., to obtain the desired Crystalline Form III.

Example 8

Preparation of Crystalline Form III

A slurry suspension of excess amount of the compound of Formula I prepared as in Example 1, was stirred in methyl MTBE, IPAc or EtOAc at 50° C. for at least 48 hrs., to obtain the desired Crystalline Form III.

Example 9

Preparation of Crystalline Form III

A slurry suspension of excess amount of the compound of Formula I prepared as in Example 1, was stirred in the mixed solvent of acetone/H$_2$O (1:1) at room temperature for at least 48 hrs., to obtain the desired Crystalline Form III.

Example 10

Preparation of Crystalline Form III

A slurry suspension of excess amount of the compound of Formula I prepared as in Example 1, was stirred in the mixed solvent of EtOAc/THF (3:1) at 50° C. for at least for 48 hrs., to obtain the desired Crystalline Form III.

Example 11

Preparation of Crystalline Form III

The compound of Formula I prepared as in Example 1 was dissolved in MTBE, IPAc, EtOAc, or the mixed solvent of EtOAc/THF or acetone/H$_2$O, and the Crystalline Form III prepared as in any one of Examples 6-8 was added as crystal seed, followed by a spontaneous precipitation to obtain the desired Crystalline Form III.

Example 12

Preparation of Crystalline Form III

The compound of Formula I prepared as in Example 1 was heated and dissolved in a solvent selected from isopropanol (IPA), 4-methyl-2-pentanone, propyl acetate, MTBE, IPAc, EtOAc, or the mixed solvent of EtOAc/THF, acetone/H$_2$O or IPA/H$_2$O (9:1), and the Crystalline Form III prepared as in any one of Examples 6-8 was added as crystal seed when the solution was cooled and crystallized, to obtain the Crystalline Form III.

Example 13

Preparation of Crystalline Form III

The compound of Formula I prepared as in Example 1 was heated to 195° C. under inert gas (N$_2$ or He), and then cooled down to room temperature, to obtain the Crystalline Form III.

Example 14

Preparation of Crystalline Form IV

The Crystalline Form I prepared as in of any one of Example 2-4 was heated to 50° C., to obtain the Crystalline Form IV, with the melting point of 189-193° C.

Example 15

Preparation of Crystalline Form IV

The compound of Formula I prepared as in Example 1 was dissolved in THF, followed by a spontaneous precipitation to obtain the Crystalline Form IV.

Example 16

Preparation of Crystalline Form IV

The compound of Formula I prepared from Example 1 was suspension stirred in H$_2$O/acetone at 50° C. for at least 48 hrs, to obtain the Crystalline Form IV.

Example 17

Preparation of Crystalline Form V

The Crystalline Form IV prepared as in any one of Example 14-16 was heated to 175° C. to obtain the Crystalline Form V, with the melting point of 192-195° C.

Example 18

Assay of HIF-PHD2 Enzyme Activity

HIF-PHD2 activity was measured using homogeneous TR-FRET technology (see also, US2008/004817; Dao J H et al., Anal Biochem. 2009, 384:213-23). To each well of a ½Area 96-well plate was added 2 µL DMSO solution of test compound and 40 µL of assay buffer (50 mM Tris PH7.4/0.01% Tween-20/0.1 mg/ml BSA/1 mM Sodium ascorbate/20 µg/ml Catalase/10 µM FeSO4) containing 600 nM full length PHD2. After a 30 min preincubation at room temperature, the enzymatic reactions were initiated by the addition of 8 µL of substrates (final concentrations of 0.2 µM 2-oxoglutarate and 0.5 µM HIF-1α peptide biotinyl-DLDLEMLAPY-IPMDDDFQL). After 2 hrs. at room temperature, the reactions were terminated and signals were developed by the addition of a 50 µL quench/detection mix to a final concentration of 1 mM ortho-phenanthroline, 0.1 mM EDTA, 0.5 nM anti-(His)$_6$LANCE reagent, 100 nM AF647-labeled Streptavidin, and 30 nM (His)$_6$-VHL-elonginB-elonginC complex. The ratio of time resolved fluorescence signals at 665 and 620 nm was determined, and percent inhibition was calculated relative to an uninhibited control sample run in parallel. For the compound of Formula I prepared from the method disclosed in Example 1 above, the IC50 was determined to be around 150 nM.

Example 19

Determination of Erythropoietin (EPO) Induction in Normal Mice

Eight-week-old male C57BL/6 mice were dosed orally with a suspension of one crystal form of the compound in 0.5% CMC at 20, 60 and 100 mg/kg. Blood samples were obtained from the orbital venous plexus 6 hours after dosing and serum was collected (see also, Robinson A, et al., Gastroenterology. 2008, 134:145-55; Hsieh M M, et al., Blood. 2007, 110:2140-7). Samples were analyzed for EPO by electrochemiluminescence-based immunoassay (MSD) according to manufacturer's instructions. The inducted EPO when the Crystalline Form III in this invention was used in suspension was determined to be above 35 folds over that of the vehicle group without induction at the dosage of 60 mg/kg.

Example 20

Stability Determination of Crystal Forms 100 mg of the compound of Formula I prepared from the method disclosed in Example 1 above (mixed crystal forms) was added into 2 mL of Ethyl Acetate and stirred at room temperature for 72 hrs. After centrifugation and drying, the resulted crystal form was determined by XRPD to be purely the Crystalline Form III. The Crystalline Form III was therefore demonstrated to be thermodynamically the more stable crystal form compared to the mixed crystal form as prepared in Example 1 at room temperature.

Example 21

Stability Determination of Crystal Forms 50 mg of the compound of Formula I prepared from the method disclosed in Example 1 above (mixed crystal forms) was added into 1 mL of Ethyl Acetate and stirred at 50° C. for 72 hrs. After centrifugation and drying, the resulted crystal form was determined by XRPD to be purely the Crystalline Form III. The Crystalline Form III was therefore demonstrated to be thermodynamically the more stable crystal form compared to the mixed crystal form as prepared in Example 1 at 50° C.

Example 22

Efficacy Studies in Adenine-Induced Renal Anemic Rats

Six-week-old male Wistar rats were divided to the control group and treatment groups. After given the standard chow for 10 days, the control group continued on the standard chow while the treatment groups were given the standard chow with the addition of 0.75% adenine for 30 days when the treatment groups developed anemia. All the groups were then switched back to the standard chow, and the treatment groups were dosed orally with vehicle or a suspension of one crystal form of the compound in 0.5% CMC-Na at 20, 40 or 80 mg/kg once a day for 4 weeks. Blood samples were obtained from the orbital venous plexus on days 0, 5, 12, 19 and 27. An Automated Hematology Analyzer MEK-6318K was used to determine hematological parameters such as erythrocyte counts (RBC), hemoglobin concentration (HGB), hematocrit value (HCT). Results for the HGB measurements were shown in Table I. It was clearly shown that dosing of Crystalline Form III of the compound has improved the HGB levels in the animals and corrected them toward normal.

TABLE I

| Group | Dose (mg/kg) | HGB (g/L) | | | | |
|---|---|---|---|---|---|---|
| | | Day 0 | Day 5 | Day 12 | Day 19 | Day 27 |
| Control | | 108.3 | 115.4 | 116.9 | 113.2 | 120.2 |
| Vehicle | | 88.0 | 64.9 | 53.1 | 58.5 | 74.3 |
| Form III | 20 | 88.0 | 60.7 | 64.3 | 73.3 | 90.7 |
| Form III | 40 | 87.4 | 69.4 | 87.2 | 89.7 | 103.6 |
| Form III | 80 | 86.8 | 76.7 | 111.0 | 122.0 | 139.0 |

Although the present invention has been described in considerable detail with reference to certain preferred versions thereof, other versions are possible. Therefore, the spirit and scope of the invention should not be limited to the description of the preferred versions described herein. Various modifications of the invention, in addition to those described herein, will be apparent to those skilled in the art from the foregoing description. Such modifications are also intended to fall within the scope of the appended claims.

What is claimed is:

1. A crystalline form of the compound of Formula I:

Formula I characterized by an X-ray powder diffraction pattern having characteristic peaks at diffraction angles 2 (±0.2°) of 12.3°, 16.6° and 25.4°.

2. The crystalline form of claim 1 characterized by the X-ray powder diffraction pattern having characteristic peaks at diffraction angles 2 (±0.2°) of 12.3°, 16.6°, 21.8°, 25.4° and 29.2°.

3. The crystalline form of claim 2, characterized by the X-ray powder diffraction pattern having characteristic peaks at diffraction angles 2 (±0.2°) of 12.3°, 13.0°, 16.6°, 18.6°, 21.8°, 25.4°, 26.9° and 29.2°.

4. The crystalline claim 1, characterized by the X-ray powder diffraction pattern shown in FIG. 3.

5. The crystalline form of claim 1 characterized by a melting point of 196-199° C.

6. A pharmaceutical composition comprising a therapeutically effective amount of a crystalline form of Formula I, and at least one pharmaceutically acceptable excipient, adjuvant or carrier, wherein the crystalline form is characterized by an X-ray powder diffraction pattern having characteristic peaks at diffraction angles 2 (±0.2°) of 12.3°, 16.6° and 25.4°; 12.3°, 16.6°, 21.8°, 25.4° and 29.2°; or 12.3°, 13.0°, 16.6°, 18.6°, 21.8°, 25.4°, 26.9° and 29.2°.

7. The pharmaceutical composition of claim 6, wherein the crystalline form has a purity of ≥85 wt %.

8. The pharmaceutical composition of claim 7, wherein the crystalline form has a purity of ≥99 wt %.

9. The pharmaceutical composition of claim 6, wherein the composition comprises 1 wt %-99 wt % of the crystalline form of Formula I.

* * * * *